United States Patent [19]

Brown et al.

[11] Patent Number: 5,573,781

[45] Date of Patent: Nov. 12, 1996

[54] METHODS AND COMPOSITIONS FOR THE TREATMENT OF A HOST WITH A CELLULAR PROLIFERATIVE DISEASE

[75] Inventors: Dennis M. Brown, Menlo Park; Richard E. Jones, Palo Alto; Richard Maskiewicz, Sunnyvale; Shawnya K. Michaels, Pacifica, all of Calif.

[73] Assignee: Matrix Pharmaceutical, Inc., Menlo Park, Calif.

[21] Appl. No.: 365,664

[22] Filed: Dec. 29, 1994

Related U.S. Application Data

[63] Continuation-in-part of Ser. No. 175,156, Dec. 29, 1993, abandoned.

[51] Int. Cl.$^6$ ............... A61K 9/14; A61K 9/50; A61K 37/00
[52] U.S. Cl. ........... 424/484; 424/502; 514/558; 514/861; 514/863; 514/864; 514/943
[58] Field of Search .................. 424/484, 502; 514/558, 861, 863, 864, 943

[56] References Cited

U.S. PATENT DOCUMENTS

| | | | |
|---|---|---|---|
| 4,879,297 | 11/1989 | Mahjour et al. | 514/282 |
| 5,051,257 | 9/1991 | Pietronigro | 424/423 |
| 5,141,751 | 8/1992 | Tomikawa et al. | 424/450 |

FOREIGN PATENT DOCUMENTS

| | | | |
|---|---|---|---|
| WO92/09272 | 6/1992 | WIPO | A61K 9/22 |

OTHER PUBLICATIONS

Theon, et al., Intratumoral Chemotherapy With Cisplatin In Oily Emulsion In Horses (Jan. 15, 1993) Javma, vol. 202:261–267.

Andrews, et al., Regional Chemotherapy In An Experimental Model Of Wilms' Tumor In Rats (1989) Cancer Chemother Pharmacol 23:31–36.

Physicians' Desk Reference (1994) Taxol, p. 670.

Livraghi, et al., US–Guided Percutaneous Alcohol Injection of Small Hepatic and Abdominal Tumors (1986) Radiology 161:309–312.

Burgener, et al., Treatment Of Experimental Adenocarcinomas By Percutaneous Intratumoral Injection Of Absolute Ethanol (Jun. 1987) Investigative Radiology, vol. 22, No. 6:472–478.

H. H. Roenigk, et al., Psoriasis, Marcel Dekker, Inc., New York, pp. 563–564. 1990.

S. Wright, et al., Psoriasis, Marcel Dekker, Inc. New York, pp. 577–578. 1991.

Matrix Pharm, Inc., Intralesional Accusite, A Phase III Clinical Study, pp. 1–4. 1994.

John W. Rollins Feb. 5, 1995.

*Primary Examiner*—John W. Rollins
*Attorney, Agent, or Firm*—Bertram I. Rowland

[57] ABSTRACT

Methods and compositions are provided for the treatment of a host with a cellular proliferative disease, particularly a neoplasia. In the subject methods, a pharmaceutically acceptable, substantially anhydrous, injectable semi-solid composition which acts as a depot for a cytostatic agent, is administered to a lesion of the disease, particularly intralesionally. The subject compositions comprise a water immiscible, fatty acid ester matrix and a cytostatic agent.

36 Claims, No Drawings

METHODS AND COMPOSITIONS FOR THE TREATMENT OF A HOST WITH A CELLULAR PROLIFERATIVE DISEASE

CROSS-REFERENCE TO RELATED APPLICATIONS

This application is a continuation-in-part of application Ser. No. 08/175,156, filed Dec. 29, 1993, abandoned, the disclosure of which is incorporated by reference.

TECHNICAL FIELD

The technical field of this invention is the treatment of a host with a cellular proliferative disease.

BACKGROUND OF THE INVENTION

Although a variety of diverse methods for the treatment of cancer, such as surgery, radiation therapy and immunotherapy, have been designed, of increasing interest in cancer therapy is the use of chemotherapeutic agents, either alone or in combination with other known treatment methods. In chemotherapy, the chemotherapeutic agents may be administered either systemically or regionally. Although systemic administration of a chemotherapeutic agent has proved effective in the treatment of some cancers, there are consequences with this mode of chemotherapeutic agent delivery. For example, in systemic administration, non-cancerous tissue and organs are exposed to the chemotherapeutic agent along with the cancerous cells. Depending on the toxicity of the particular chemotherapeutic agent employed, the consequences of systemic delivery may outweigh the therapeutic benefit of the agent.

Furthermore, some chemotherapeutic agents are poorly water soluble. Thus., to be administered intravenously (one particular mode of systemic administration) they must be diluted in large volumes of an aqueous vehicle. However, dilution of the drug in this manner can limit the dosage level of the drug that can be achieved in the host blood stream or in proliferative disease tissue. Other factors which can adversely affect the dosage level of drug which is achieved in the blood stream include metabolism, chemical instability and in situ precipitation of the drug.

In view of these considerations, there is increasing interest in the regional administration of chemotherapeutic agents. Although methods of regional administration of such agents have been studied, the results have not been entirely satisfactory. For example, in some instances the chemotherapeutic agents have been found to diffuse too readily from the vehicle in which they are administered and the region of administration into other regions of the host, thereby causing toxic side effects. Furthermore, problems with stability and bioavailability of drug in these regional delivery vehicles have been experienced.

Thus, there is a continued need for the development of improved delivery vehicles, as well as methods of using these vehicles, for the-regional treatment of hosts with a cellular proliferative diseases.

Relevant Literature

U.S. patents describing the intratumoral delivery of antineoplastic agents include U.S. Pat. No. 5,051,257. RE-33,375 describes the use of a collagen matrix as a chemotherapeutic delivery vehicle.

Regional chemotherapy consisting of intratumoral injections of cisplatin in a sesame oil-water emulsion delivery vehicle is described in Theon et al., J.A.V.M.A. (1993) 202: 261–267. Regional chemotherapy of Wilms' tumors in rats is described in Cancer Chemother. Pharmacol. (1989) 23: 31–36. Intratumoral administration of ethanol in the treatment of neoplasia is described in Burgener et al., Investigative Radiology (1987) 22:472–478 and Livraghi et al., Radiology (1986) 161: 309–312.

Non-Aqueous, intraperitoneal drug delivery vehicles are described in Ansel, Introduction to Pharmaceutical Dosage Forms (Lea & Freiberger, Philadelphia) (1976) p246; Hoover, Dispensing of Medication (Mack Publishing Co.) (1976); and Targo & King, Sterile Dosage Forms, Their Preparation and Clinical Application (Lea & Freiberger, Philadelphia)(1987) pp 17–24.

SUMMARY OF THE INVENTION

Methods and compositions are provided for the treatment of a host with a cellular proliferative disease, particularly a neoplasia. In the subject methods, pharmaceutically acceptable, substantially anhydrous, injectable, semi-solid compositions which act as depots for a cytostatic agent, are administered at the site of a lesion of the disease, particularly intralesionally. The subject compositions comprise a water immiscible, fatty acid ester matrix and a cytostatic agent.

DESCRIPTION OF THE SPECIFIC EMBODIMENTS

Methods and compositions are provided for the treatment of a host with a cellular proliferative disease, particularly a neoplasia. In the subject methods, carrier compositions comprising pharmaceutically acceptable, substantially anhydrous, injectable, semi-solid compositions which act as depots for a cytostatic agent are administered at the site of a lesion of the disease, particularly intralesionally. In further describing the subject invention, the subject compositions will be described first followed by a description of their use in the treatment of a host with a cellular proliferative disease.

The first component of the subject carrier compositions is a water immiscible lipid matrix. The matrix contributes to the physical characteristics of the subject compositions, e.g. viscosity, which are described in greater detail below. Lipid matrices suitable for use in the subject invention will have minimal water solubility at standard temperature and pressure (STP) and normally under physiologic conditions as well. The subject lipid matrices will be no more than about 13% w/v soluble in water, usually no more than about 8% w/v soluble in water, and preferably less than about 1% w/v soluble in water.

Although any suitable physiologically acceptable lipid matrix material may be employed, usually the matrix material will be fatty acid ester compositions, having the desired flowable and viscosity characteristics, either as a natural characteristic or as a result of additives. Suitable lipid compositions will comprise fatty acid esters, either a single fatty acid ester or a mixture of fatty acid esters, which are biodegradable in the host, by themselves or in combination with one or more physiologically accceptable thickening agents, particularly fatty acid salts or synthetic and/or longer chain fatty acid esters, e.g. waxy esters. Suitable fatty acid ester compositions will comprise a single or mixture of fatty acid esters, and may comprise two or more different fatty acid esters, usually not more than ten different fatty acid esters. Suitable fatty acid esters include mono-, di- and tri-glycerides, as well as mono- and dibasic acid esters, e.g. ethyl oleate, isopropyl myristate, etc., where the carboxylic acid group will usually have at least 6, more usually at least 8 carbon atoms, preferably at least about 12 carbon atoms, may be saturated or unsaturated, usually having not more than 3 sites of ethylenic unsaturation per acid moiety, and the fatty acid esters will have at least 8 carbon atoms and not more than about 60 carbon atoms, usually not more than about 50 carbon atoms. Of particular interest are glycerides having fatty acids of from about 12 to 24 carbon atoms, saturated or unsaturated, naturally occurring or synthetic. The alcohols will usually have from about 1 to 6, usually one to five, more usually 1 to 3 hydroxyl groups and not more than two ether groups and will usually be from 2 to 6, more usually 2 to 3 carbon atoms. The fatty acid esters of the subject invention will not include esters which are modified with additional functional groups which increase the water solubility properties of the esters, e.g. such as polyoxyethylated castor oil or other alkyleneoxy modified fatty acid esters. The fatty acid esters may be added as partially pure fractions or complex mixtures such as saturated or partially saturated glycerides, e.g. oils and fats. Any carboxylic acid ester oil which is physiologically acceptable can be employed as the matrix component, where the oil may be a single or combination of oils, which may or may not be partially hydrogenated. Specific physiologically acceptable oils of interest include vegetable oils, such as sesame, peanut, soybean, cottonseed, corn, olive, persic, castor, and the like. See Spiegel, J. Pharm. Sci. (1963) 52: 917.

The carrier composition for the cytostatic agent will have a lipid matrix component and optionally an alkanol component. The lipid component may serve as the major component of the cytostatic composition or may be mixed with a lower alkanol of from 2 to 3 carbon atoms, e.g. ethanol and isopropanol, where the alkanol may comprise a substantial portion of the carrier composition, as well as the cytostatic composition. Therefore, there will be two primary ranges for the amount of lipid: (a) in the absence of a major amount of alkanol; and (b) in the presence of a major amount of alkanol.

The carrier lipid matrix component will comprise from about 1 to 99.5 w/v % of the cytostatic composition, usually from about 5 to 98 w/v %, and from about 2 to 100 w/v %, usually 2 to 95 w/v %, preferably 10 to 95 w/v % of the carrier composition. The lipid matrix component in the absence of a significant amount of alkanol will generally be from about 50 to 99.5%, usually from about 65 to 99.5%, more usually from about 75 to 98 w/v % of the cytostatic composition. When a significant amount of alkanol is present, the matrix component will usually be at least about 2 w/v %, more usually at least about 5 w/v %, generally from about 10 to 50 w/v % of the composition, more usually 10 to 40 w/v % and preferably no more than about 30 w/v % of the total cytostatic composition. The alkanol in the carrier composition will usually be in the range of about 2 to 98 v/v %, frequently 30 to 95 v/v %. For the most part the carrier composition will consist of from about 10 to 90 w/v % of the lipid matrix and 90 to 10 w/v % of the alkanol, frequently from about 10 to 40% of the lipid matrix and 90 to 60 w/v % of the alkanol, preferably about a 30:70 ratio.

In some instances, the fatty acid ester matrix component may comprise an additional agent which serves to thicken the matrix, thereby providing for the injectable, semi-solid nature of the composition, as described below, whose weight will be included in the ranges provided about for the matrix component. Any thickening agent which does not adversely affect the pharmaceutically acceptable nature of the composition may be employed, nor interfere with the purpose of desired characteristics of the cytostatic composition. Thickening agents of interest include: aluminum monostearate, stearic acid, cetyl/stearyl alcohol, guar gum, methyl cellulose, hydroxypropylcellulose, tristearin, cetyl wax esters, polyethylene glycol 4000, and the like. When a thickening agent is included in the subject composition, the thickening agent may be present in ranges from 0.5 to 40% w/v, usually from 1 to 36% w/v of the lipid matrix component of the carrier composition.

The particular matrix employed in a cytostatic composition will depend, at least in part, on the cytostatic agent to be administered in the composition, certain combinations of matrix and agent being more efficacious than others. Particular matrix and agent combinations can be determined empirically and optimized in accordance with conventional procedures.

The next component of the subject composition is the cytostatic agent. A wide variety of cytostatic agents may find use in the subject invention. By cytostatic is meant that the agent tends to retard cellular activity and multiplication, and is preferably cytotoxic. The employed agents may or may not be stable in an aqueous environment. Furthermore, the agents may or may not be water soluble, but will usually be insoluble or only slightly soluble in aqueous solvents. As used herein, a water insoluble cytostatic agent is less than about 0.1% w/v soluble in water (less than about 0.1 g dissolves in 100 ml of water at STP). A poorly water soluble cytostatic agent is less than about 5 % w/v soluble in water. Of course, a selected drug may be chemically modified by ways known in the art to modulate solubility in the disclosed compositions, bioavailability, etc.

Exemplary cytostatic agents include alkylating agents, enzyme inhibitors, proliferation inhibitors, DNA synthesis inhibitors, lytic agents, DNA intercalators, antimetabolites and the like. Illustrative agents include steroids, paclitaxel, ionomycin, etoposide, nitrosoureas such as carmustine (BCNU), doxorubicin, daunorubicin, actinomycin D, meclorethamine, busulfan, CCNU, Me-CCNU, chlorambucil, cactinomycin, carzinophilin, chlornaphazine, 6-chloropurine, campothecin, mitomycin, lomustine (CCNU), semustine (Me-CCNU), cantharidin, camptothecin, cisplatin, carboplatin, ricin, pseudomonas exotoxin, fluorouracil, interferons (e.g. ,γ, γ-1a, β, α, etc.), interleukins (e.g. 2 and 4), TNFα and -β, vincristine, mitotane melphalan, methchlorethamine, plicamycin, nitracine, nitoxantrone, methotrexate, nogalamycin, streptonigrin, streptozocin, tegafur, tetramin, testolactone demecolcine, dactinomycin, etc., particularly lipophilic species. See Carter and Livingston, Drugs Available to Treat Cancer. In Principles of Cancer Treatment (Carter et al. eds.) Chap 10, pp 111–145, 1982. McGraw-Hill Inc, NY. The anhydrous nature of the subject compositions makes the compositions particularly suited for the delivery of insoluble or sparingly soluble agents, as well as agents that contain functional groups which may adversely interact with the components of an aqueous delivery vehicle. Insoluble, or only slightly soluble, agents of interest include amsacrine, biantrene hydrochloride, camostat mesylate, campothecin, carmustine, enocitabine, etoposide, epirubicin hydrochloride, fludarabine phosophate, flutamide, fotemustine, idarubicin hydrochloride, ionomycin, onidamine, mitomycin, mitoxantrone hydrochloride, nilutamide, paclitaxel, pirarubicin, toremifene, vinorelbine, didemnin, bactracyclin, mitoquidone, penclomedine, phenazinomycin, U-73975, saintopin, 9-aminocamptothecin, amonafide, merbarone and the like. Agents containing reactive functional groups include mitomycin C, cisplatin, mechlorethamine, daunorubicin, carmustine, pyrazine diazohydroxide, fumagillin analog FR-111142, rhyzoxin, dynemicin A, chlorambucil, semustine, and the like. Of particular interest are the drugs in their free base form, as distinct from their salt form.

In preparing the subject cytostatic compositions, the cytostatic agent may be combined directly with the delivery vehicle or vehicle component or first solubilized, as may be necessary and is known in the art, in a solvent and then combined with the delivery vehicle. Solvents of interest are anhydrous and typically organic, such as dimethyl adipate, DMSO, any of the alkanols discussed below, and the like.

The concentration of the cytostatic agent in the subject compositions will vary depending on the particular cytostatic agent, the type of tumor to be treated, the projected treatment regimen, dosage schedule and the like. Usually the cytostatic agent in the composition will be present in an amount sufficient to slow the cellular growth of the proliferative disease being treated, generally ranging from about 0.5 to 50 mg/ml, and more usually ranging from about 1 to 40 mg/ml.

The next component of the subject compositions is optional, but preferred, and is a diluent. The diluent, in addition to the matrix, will contribute to the physical properties of the composition, as will be described below.

Of particular interest are diluents which, in addition to modifying cytostatic agent solubility and/or matrix viscosity, exhibit cytostatic activity in their own right. When such cytostatic diluents are employed, the diluent may serve a number of purposes. In some instances, the cytostatic agent may be the only cytostatic agent in the composition. In other instances, the cytostatic diluent may contribute to the cytostatic activity of the composition in an additive manner in conjunction with the agent. In other instances, a synergistic effect may be realized between the cytostatic diluent and the agent. Diluents of interest are alkanol diluents, such as ethanol, isopropanol, butanol, hexanol, octanol and the like, particularly ethanol and isopropanol. When present in the carrier composition, the diluent will usually comprise at least about 10 (v/v) %, frequently at least about 20 (v/v) %, more usually at least about 30 (v/v) % and up to about 98 (v/v) % of the carrier compositions. Thus, the total diluent may range from 5 to 95 (v/v)%, usually 90 (v/v) %, of the carrier composition, where the alkanol will usually range from 10 to 90 (v/v) % of the carrier composition, and more usually will range from 20 to 80 (v/v) % of the composition, and preferably will be about 50 to 75 (v/v) % of the composition.

In addition to the above components, other compounds, agents or excipients may be included in the subject compositions with beneficial result. The compositions may comprise effector agents which enhance the efficacy of the compositions, either directly, by interacting with a selected cytostatic agent or cellular target, or indirectly by affecting the host responsiveness. For example, chelators such as EDTA or EGTA, may be used to complex and extend the half-life of the agent directly and/or alter local cellular permeability, antioxidants may find use in extending the activity of the agent, while vasomodulators, immune modulators, etc. are used to affect host responsiveness. Of particular interest are effectors which restrict regional vasculature, e.g. vasoactive agents, either as to growth and/or passage opening, e.g. vasoconstrictive or sympathomimetic agents. These effectors include catechol amines, e.g. epinephrine and its borate salt, nor-epinephrine, dipivefrin, ephedrine, ergot alkaloids, prostaglandins, angiotensin, and the like. Other effectors for affecting tissue architecture include enzymes which can injure the stroma, such as the peptidase papain, chymopapain, trypsin, amylase, collagenase and chymotrypsin. Compounds affecting cellular permeability may be employed, such as EDTA, phospholipids, non-ionic detergents, e.g. Polysorbate 80, amphotericin B, dimethylsulfoxide, glycosides, e.g. saponin, and anaesthetics such as procaine. Compounds which modulate the immune response include adjuvants, interferons, lymphokines such as IL-2, TNF, etc.; those which enhance cytotoxicity include radioactive pellets; radiation sensitizers, e.g. methylated xanthines; bioreductive agents, etc. An effective dosage of cytostatic agent is that which enhances the therapeutic affect of the subject compositions. Effector compounds may be provided at the minimum amount required to achieve optimal efficacy. The concentration of effector agent in the composition will usually range from about $1\times10^{-3}$ to 5 mg/ml, more usually from about 0.01 to 2.5 mg/ml. For many effectors, e.g. epinephrine, the administered amount is generally in the range of about 1–100 µg/kg body weight. Effectors of particular interest include epinephrine and its borate salt and ephedrine Additional minor components are often included in the subject compositions for a variety of purposes. These components will for the most part impart properties which enhance cytostatic agent retention at the site of administration, protect the stability of the composition, control the pH, further reduce cytotoxic agent diffusion from the site of administration, etc. Illustrative components include buffers, viscosity enhancing agents, etc. These components are generally present in less than about 10 weight % of the total composition, usually less than about 5 weight %, more usually individually less than about 0.5 weight % and more than about 0.001% of the total composition. See Hoover, Dispensing of Medication (Mack Publishing, 1976).

The various components described above are combined to produce a pharmaceutically acceptable, cytostatic composition. By pharmaceutically acceptable is meant that the composition is physiologically acceptable when administered to the host in accordance with the subject method. Pharmaceutically or physiologically acceptable compositions are compositions which are stable, sterile, free of pyrogens, biodegradable and the like. See Ansel, Introduction to Pharmaceutical Dosage Forms (Lea & Freiberger, Philadelphia)(1976).

For the most part, the subject compositions are injectible, semi-solid compositions. In other words, the compositions are flowable such that they may be injected into a lesion, but possess sufficient viscosity to allow retention of the cytostatic agent at an effective dosage at the site of administration for a reasonable period of time, usually in excess of 6 hours. The viscosity of the compositions will range from 5000 to 50,000 centipoise (cps), where cps is measured at standard temperature and pressure (STP), at a low shear, typically at no more than 30/sec. That is the subject compositions can be readily injected by means of a syringe into a lesion and can be mixed by means of two syringes and a mixing adaptor into which the syringes can introduce and withdraw material.

The subject compositions are also substantially anhydrous, whereby substantially anhydrous is meant that the delivery vehicles are not more than about 5 weight %, preferably less than about 1 weight %, and more preferably less than about 0.2 weight % water.

The nature of the subject compositions provides that the compositions act as a depot for the cytostatic agent. The compositions described herein are generally capable of forming uniform, stable dispersions, e.g. solubilizing the selected drug at concentrations exceeding 0.01%, preferably exceeding 0.1%, more preferably exceeding 1% w/v of the composition. In using the subject compositions, the lipid matrix mass is retained at the injection site and the dispersed drug diffuses from the injected composition into the lesion or tumor of the cellular proliferative disease.

In addition to the above compositions, it has also been found that administration of a cytostatic agent in a water-immiscible alkanol with or without a water immiscible lipid matrix can enhance the cytostatic activity of the particular agent. Water immiscible alkanols, when employed as delivery vehicles in this manner, will typically be C4 or higher, generally having from 4 to 10 carbons (tert-butanol is excluded because it is water miscible—of infinite water solubility at STP); may be primary, secondary or tertiary, preferably primary; and generally contain one to two hydroxyl groups. Preferred alkanols contain only carbon atoms and one or two hydroxyl groups and have low toxicity when used in the subject method. Particular alkanols which find use as delivery vehicles include butanol, hexanol and octanol. Where an alkanol is employed as a delivery vehicle, the cytostatic agent will be present in the alkanol delivery vehicle in amounts ranging from about 0.5 to 50 mg/ml, usually from about 1 to 40 mg/ml.

The subject compositions having been described, their use in the treatment of a host with a cellular proliferative disease will now be discussed in greater detail. The subject compositions find particular use in the treatment of hosts with cellular proliferative diseases characterized by lesions or solid tumors. In the subject method, the cytostatic compositions are administered to any convenient site of the host where the composition may act as a depot for the cytostatic agent. Typically the composition will be administered directly at the site of the lesion or tumor of the disease, particularly intralesionally. Although the composition may be administered to a single site of the tumor, usually the composition will be administered to multiple sites of the tumor. The route of administration will be any convenient route by which the subject cytostatic compositions can be administered directly to the tumor. Thus, the composition may be administered by syringe needle, catheter, trochar, and the like.

Therapies which employ the subject compositions and methods may vary depending on the particular host, the nature of the cellular proliferative disease, the size of the lesion and the like. Thus, the cytostatic composition may be administered once in a particular therapy, where therapy intends the entire treatment of the host, or several times, where the interval between administrations may be a matter of minutes, hours, days, or even months.

In the subject method, the volume of distribution, concentration distribution and total dosage of agent in the composition administered to the host are controlled by varying the compositions and/or the method of administration. This is especially important when using drugs with high toxicity, limited stability in vivo, high cost, etc. As indicated above, the drug concentration, diluent selection and additives may be varied in relation to the particular indication, host condition, growth stage of tumor, etc. In addition, the previously mentioned parameters are influenced by providing a single injection or multiple injections into separate regions of the tumor, by controlling the localized temperature and blood circulation at the site of administration, etc., as is known in the art. Generally, the volume and concentration of the subject compositions administered into the tumor mass should be sufficient to contact as many tumor cells as possible with a lethal dosage of agent while minimizing exposure to and/or necrosis of surrounding and/or sensitive normal tissue. The volume of composition administered to the tumor in a particular administration may range from 10 to 500 µl, usually 50 to 200 µl per 100 mm$^3$ of treated tissue. The dose of cytostatic agent delivered to a tumor site in a particular administration may range from about 0.01 to 200 mg/kg of host, and will usually range from about 0.1 to 100 mg/kg of host, substantially varying with the particular agent, the nature of the composition and tumor, the host and the like.

Although the effectors may be included within the subject compositions for simultaneous administration, the effectors may also be administered shortly after the subject compositions. When the effector agent is administered after administration of the composition, the effector agent will be administered within about 8 hours, preferably within about 4 hours, more preferably within about 2 hours, and most preferably within about 1 hour. Alternatively, the effector compounds may be administered prior to administration of the cytostatic composition. For instance, it may be advantageous to "prime" the host with an effector agent, e.g. epinephrine, within about 60 minutes, preferably within about 10 minutes, more preferably within about 2 minutes prior to the administration of the subject compositions.

The subject method may be used to treat a wide variety of hosts. Hosts amenable to treatment using the subject method include mammalian hosts, such as domestic animals, e.g. pets and livestock, rare or exotic animals, and humans. Tumors or lesions amenable to the subject method of treatment include solid malignant tumors of the lung, breast, colon, rectum, ovaries, stomach, pancreas, uterus, testicles, brain, liver, head and neck, prostrate and the like. Typically, therapeutic gain can be realized with tumors greater than about 50 mm$^3$, particularly with tumors greater than 100 mm$^3$, and more particularly with tumors greater than 200 mm$^3$.

The effectiveness of the disclosed methods may generally be characterized as reducing the severity of toxicity to tissue surrounding the lesion, dose limiting normal tissues and reducing tumor burden, as well as delaying growth and tumor progression. The disclosed methods generally result in an inhibition in the growth of the neoplasia as compared with no treatment, systemic treatment or intralesional treatment with the delivered drug in a water-miscible vehicle.

The following examples are offered by way of illustration and not by way of limitation.

EXPERIMENTAL

The following are water immiscibel lipid mixtures representing Anhydrous Delivery Vehicles (ADV) compositions:

| | |
|---|---|
| ADV8 | commercially available partially hydrogenated soybean and cottonseed oils |
| ADV 9 | 3,000 mg tristearin |
| | 12,000 µl peanut oil |
| ADV 12 | 12,750 µl peanut oil |
| | 2,250 mg aluminum monostearate |
| ADV 13 | 12,750 µl sesame oil |
| | 2,250 mg stearic acid |
| ADV 14 | 12,000 µl sesame oil |
| | 3,000 mg cetyl/stearyl alcohol (50:50) |
| ADV 15 | 10,800 µl sesame oil |
| | 2,250 mg steric acid |
| | 1,950 mg triacetin |

Example 1. The Cytostatic Activity of Ethanol and Butanol in ADV Compositions

Transplantable experimental murine fibrosarcomas ($2\times10^5$ RIF-1 cells) were grown intradermally in the flanks of 3 month old female C3H mice (Massachusetts General, Boston, Mass.). When the tumors reached a volume of 100 mm$^3$, the mice were assigned randomly to each experimental group (5 mice per group).

Ethanol and butanol/ADV compositions were prepared as described in Tables 1 & 2 with an ethanol:ADV ratio of 70:30 (v/v). The compositions were injected intratumorally (hereinafter i.t.). After treatment, the growth of the tumors was monitored three times per week by caliper measurements of three perpendicular diameters of the tumor and calculating tumor volume from the formula:

$$V = \pi/6 \times D_1 \times D_2 \times D_3,$$

where $D_{1-3}$ is in mm.

The tumors were followed until they reached 4 times their treatment size or up to 30 days after treatment (tumor growth delay, TGD), whichever came first. The data is also expressed as the ratio of the tumpor growth delay of the treated tumor (TGD) over the untreated control group (CTGD). Increasing values of this ratio indicate increased antitumor response. The data is presented in Tables 1 & 2, below.

TABLE 1

| Cytostatic Alcohol (Injection Volume of 50 μl intratumorally on Day 0). | Anhydrous Delivery Vehicle | Tumor growth delay of treated tumor (days)(TGD)/ untreated control growth (CTGD) |
|---|---|---|
| Ethanol | None | 1.39 |
| Ethanol | ADV 8† | 1.70 |
| Butanol | None | 1.11 |
| Butanol | ADV 8† | 2.08 |

†A commercially available mixture of partially hydrogenated soybean and cottonseed oils. The % w/v for alkanol to ADV8 is 70:30.

The results of Table 1 indicate that the cytostatic activity of both ethanol and butanol is enhanced when the alcohol is administered in a composition comprising ADV 8.

TABLE 2

| Composition | Volume of Composition Injected | Days to 4 × Orig. Volume Size ± SE | |
|---|---|---|---|
| | | treated | untreated* |
| Untreated (control) | none | 6.3 ± 0.1 | |
| 70% Ethanol (aqueous) | 150 μl | 11.6 ± 1.3 | |
| 70% Ethanol (aqueous) | 200 μl | 13.4 ± 3.1 | |
| 70% Ethanol (aqueous) | 250 μl | 16.6 ± 1.3 | |
| ADV 9 - Ethanol (30/70) | 50 μl | 12.0 ± 0.7 | 7.0 ± 0.7 |
| ADV 9 - Ethanol (30/70) | 150 μl | 16.5 ± 1.0 | |
| ADV 9 - Ethanol (30/70) | 200 μl | 19.3 ± 1.3 | |
| ADV 9 - Ethanol (30/70) | 220 μl | 17.9 | |
| ADV 9 - Ethanol (30/70) | 250 μl | 18.0 | |

*untreated = untreated contralateral tumor

The results of Table 2 demonstrate that 70% ethanol compositions that comprise ADV 9 have enhanced cytostatic activity over aqueous 70% ethanol compositions.

Example 2. Paclitaxel-ADV i.t. Compositions

Paclitaxel compositions for i.t. injection were prepared as indicated in Tables 3 & 4 below. In each case, the composition was administered directly to the RIF-1 tumor, as described in Example 1 above.

TABLE 3

Administration of 50 μl of Paclitaxel Composition

| Dose of Pac-litaxel in mg/kg | Composition | 4 × Tumor Growth (days) | | TGD/ CTGD |
|---|---|---|---|---|
| | | treated | untreated | |
| control | none | 6.5 ± 0.4 | | |
| 12 | Agent in Aqueous Susp.‡ | 8.4 ± 1.0 | 6.8 ± 0.3 | 1.3 |
| 12 | Agent in ADV 9 (peanut oil/20% tristearin) | 9.0 ± 0.5 | 7.9 ± 0.5 | 1.4 |
| 12 | Agent in ADV 12 (peanut oil/15% aluminum monostearate) or (255 μl peanut oil/45 mg aluminum monostearate) | 6.9 ± 0.6 | 5.8 ± 0.5 | 1.1 |
| 12 | Agent in ethanol/ ADV 12; 70/30 v/v | 11.0 ± 1.1 | 6.8 ± 0.8 | 1.7 |
| 12 | Agent in ADV 13 (sesame oil/15% stearic acid) | 10.1 ± 1.2 | 5.9 ± 0.7 | 1.6 |
| 12 | Agent in ADV 14 (sesame oil/20% cetyl/stearyl alcohol (50:50)) | 6.5 ± 0.5 | 7.4 ± 0.5 | 1.0 |
| 12 | Agent in ADV 15 (sesame oil/15% stearic acid + 13% triacetin) | 10.6 ± 1.6 | 6.6 ± 0.6 | 1.6 |

TGD/CTGD = Ratio of Treated Tumor Growth Delay (Days) to Control Tumor Growth Delay (Days)
‡= Polysorbate 80 (0.075% w/v)/NaCMC (1% w/v) in saline

TABLE 4

| Cytostatic Agent | Dose mg/kg | Composition | TGD/CTGD |
|---|---|---|---|
| Paclitaxel | 10 | Sesame Oil | 1.0 |
| Paclitaxel | 10 | Saline | 0.8 |
| Paclitaxel | 15 | ethanol/ADV 9 (70:30) | 2.4 |
| Paclitaxel | 15 | ethanol | 1.6 |
| Paclitaxel | 15 | CremEL/ethanol (50/50) | 1.0 |
| Paclitaxel | 15 | CremEL/ethanol (15/15) | 1.1 |

The results in Table 3 demonstrate that when paclitaxel is administered i.t. in a composition comprising either ADV 9, ADV 13 or ADV 15, the cytostatic activity of paclitaxel is enhanced relative to an aqueous suspension. The results also indicate that compositions comprising ADV 12 and ethanol further enhance the cytostatic activity of paclitaxel. The results in Table 4 indicate that the activity of paclitaxel in ethanol plus ADV9 exceeds that in ethanol or lipid alone (sesame oil), in saline or in a mixture of ethanol and a surfactant (CremEL/ethanol)

Example 3. Mechlorethamine-ADV Compositions

Mechlorethamine compositions for i.t. injection were prepared and dosed as described in Tables 5 & 6. The compositions were injected i.t. into RIF-1 tumors, as described in Example 1. The results are provided in Tables 5 & 6.

TABLE 5

| Dose of Mechlor-ethamine in mg/kg | Delivery Vehicle | TGD/ CTGD | 4 × Tumor Growth (days) treated | untreated |
|---|---|---|---|---|
| control | none | | 6.3 ± 0.1 | |
| 0.2 | Ethanol | 2.1 | 13.0 ± 0.9 | 6.6 ± 0.2 |
| 0.2 | Ethanol/ADV 9 (70:30) | 2.6 | 16.6 ± 1.0 | 7.3 ± 0.7 |
| 0.2 | Ethanol/ Epinephrine | 2.7 | >17.3 ± 1.9 (1 cure) | 7.0 ± 0.6 |
| 0.2 | Ethanol/ Epinephrine/ ADV 9 | 3.1 | 19.8 ± 1.5 | 7.0 ± 0.7 |

TGD/CTGD = Ratio of Treated Tumor Growth Delay (Days) to Control Tumor Growth Delay (Days)

TABLE 6

| Dose of Mechlor-ethamine (mg/kg) | Composition | TGD/CTGD |
|---|---|---|
| 0.02 | agent in 100% ethanol | 1.69 |
| 0.02 | agent in ethanol:ADV 8 (70:30) | 1.95 |

The results in Tables 5 and 6 indicate that mechlorethamine compositions (solutions in ethanol) which contain ADV 8 or ADV 9 have enhanced cytostatic activity. Inclusion of the effector agent epinephrine in these compositions further enhances the cytostatic activity of the mechlorethamine (Table 5).

Example 4. The Cytostatic Activity of Ionomycin in ADV 8 Compositions

Ionomycin compositions suitable for i.t. injection were prepared and dosed as described in Table 7. The compositions were injected into RIF-1 tumors as described in Example 1. The results are provided in Table 7.

TABLE 7

| Dosage of Ionomycin in mg/kg | Composition | TGD/CTGD |
|---|---|---|
| 8 | agent in 100% ethanol | 2.4 |
| 8 | agent in ethanol:ADV 8 (70:30) | 2.55 |

TGD/CTGD = Ratio of Treated Tumor Growth Delay (Days) to Control Tumor Growth Delay (Days)

The results in Table 7 show that i.t. injection of a composition comprising ionomycin and ADV 8 delays tumor growth to a greater extent than an i.t. injection of ionomycin in 100% ethanol.

Example 5. The Cytostatic Activity of Etoposide in an ADV 9 Composition

Etoposide compositions were prepared and dosed as described in Table 8. 50 μl of each composition were injected into a RIF 1 tumors, as described in Example 1. The results are provided in Table 8.

TABLE 8

| Dosage of Etoposide in mg/kg | Composition | TGD/ CTGD |
|---|---|---|
| 24 | 12 mg agent/ml with 1.2 mg/ml citric acid, 18 mg/ml benzyl alcohol, 48 mg modified polysorbate 80/tween 80, 390 mg/ml poly- | 2.03 |

TABLE 8-continued

| Dosage of Etoposide in mg/kg | Composition | TGD/ CTGD |
|---|---|---|
| | ethylene glycol 300 and 0.4 ml absolute ethanol | |
| 24 | 12 mg agent/ml with 1.2 mg/ml citric acid, 18 mg/ml benzyl alcohol, 48 mg modified polysorbate 80/tween 80, 390 mg/ml poly-ethylene glycol 300, 0.3 ml ADV 9 and 0.1 ml absolute ethanol | 2.15 |

The results indicate that when etoposide is administered in a composition containing ADV 9, the delay in tumor growth is enhanced.

Example 6. The Activity of 5 Fluorouracil (5-FU) -ADV Compositions

Compositions of 5-FU were prepared as described in Table 9. The concentration of 5-FU in each of the compositions was 12 mg/ml. 50 μl of each composition were injected intratumorally into RIF-1 tumors, as described in Example 1.

TABLE 9

| Dose of 5-FU in mg/kg | Composition | 4 × Tumor Growth (Days) treated | untreated |
|---|---|---|---|
| none | untreated control | 6.5 ± 0.4 | |
| 24 | 5-FU solution | 13.2 ± 0.3 | 10.4 ± 1.0 |
| 24 | agent in ADV 9 (peanut oil/20% tristearin) | 10.8 ± 0.6* | 7.7 ± 0.5 |
| 24 | agent in ADV 12 peanut oil/15% aluminum mono-stearate) | 17.3 ± 3.4** | 7.6 ± 0.3 |
| 4 | agent in ADV 12/ ethanol (70/30 v/v) | 15.1 ± 1.5 | 7.1 ± 0.8 |
| 24 | agent in ADV 13 (sesame oil/15% stearic acid) | 18.3 ± 1.2 | 10.8 ± 0.6 |
| 24 | agent in ADV 15 (sesame oil/15% stearic acid + 13% triacetin) | 13.4 ± 0.7 | 8.7 ± 0.4 |

*one animal found dead on day 2
**one animal had tumor less than the 4× endpoint on day 30.

The results in Table 9 indicate that inclusion of ADV 12, ADV12 plus ethanol, or ADV 13 in 5-FU i.t. compositions enhances the cytostatic activity of 5-FU, relative to simple aqueous solution of the drug. All ADV compositions of 5-FU showed cytostatic activity as well as localization of effect in the treated versus the untreated tumors.

Example 7. The Cytostatic Activity of Various Cantharidin Compositions

Cantharidin compositions for i.t. injection were prepared and dosed as indicated in Table 10. The concentration of cantharidin in each of the compositions was 2.5 mg/ml. 50 μl of each composition were injected i.t. into RIF -1 tumors as described in Example 1.

TABLE 10

| Dose of Cantharidin in mg/kg | Composition | 4 × Tumor Growth (Days) treated | untreated |
|---|---|---|---|
| control | | 5.9 ± 0.2 | |
| 5 | agent in Ethanol | 14.8 ± 1.1 | 6.8 ± 0.3 |

TABLE 10-continued

| Dose of Cantharidin in mg/kg | Composition | 4 × Tumor Growth (Days) | |
|---|---|---|---|
| | | treated | untreated |
| | solution | | |
| 5 | agent in Epinephrine (0.1 mg/ml)/ethanol solution | 16.4 ± 1.7 | 6.7 ± 0.7 |
| 5 | agent in Epinephrine (0.1 mg/ml)/70% ethanol/ADV 9 | 18.2 ± 1.8 | 6.7 ± 0.2 |
| 5 | Epinephrine injected 1 min prior to injection of Cantharidin in ethanol* | >19.8 ± 2.2 * | 5.9 ± 0.2 |
| 5 | Epinephrine injected 1 min prior to injection of Cantharidin in ethanol/ADV9** | >18.3 ± 2.0 * | 7.4 ± 0.2 |

* 1 cure

The results of Table 10 demonstrate that inclusion of ADV9 in the cantharidin/epinephrine/ethanol composition enhances the cytostatic activity of the cantharidin.

Example 8. Paclitaxel/Mechlorethamine- ADV Compositions

To study the effect of ethanol content in agent/ADV compositions has on the cytostatic effect of ethanol, paclitaxel and mechlorethamine compositions were prepared as described in Table 11. 50 μl of each composition were injected into RIF-1 tumors, as described previously in Example 1.

TABLE 11

| Dose of active agent in mg/kg | Composition | 4 × Tumor Growth (Days) | |
|---|---|---|---|
| | | treated | untreated |
| none | untreated control | 7.7 ± 0.4 | |
| 12 | Paclitaxel in ethanol solution | 11.9 ± 0.5 | 8.0 ± 0.2 |
| 12 | Paclitaxel in ethanol 30%/ADV 12. | 12.4 ± 0.4 | 7.9 ± 0.4 |
| 12 | Paclitaxel in ethanol 70%/ADV 12 | 16.4 ± 3.1 | 7.8 ± 0.3 |
| 12 | Paclitaxel in ethanol 90%/ADV 12 | 15.2 ± 1.0 | 7.7 ± 0.5 |
| 0.2 | Mechlorethamine HCl in ethanol solution | 16.4 ± 3.4 | 8.5 ± 0.5 |
| 0.2 | Mechlorethamine HCl in 30% ethanol/ADV 12 | 15.8 ± 3.0 | 7.6 ± 0.5 |
| 0.2 | Mechlorethamine HCl in 70% ethanol/ADV 12 | 20..8 ± 2.1 | 7.9 ± 0.1 |
| 0.2 | Mechlorethamine HCl in 90% ethanol/ADV 12 | 17.3 ± 1.2 | 7.7 ± 0.9 |

The results in Table 11 demonstrate that mixtures of ADV12 and ethanol yield greater cytostatic activity than solutions of paclitaxel or mechlorethamine in ethanol alone, and that enhancement of the cytostatic activity of agent/ADV compositions is most enhanced in compositions comprising 70% ethanol.

Example 9. The Cytostatic Effect of ADV Compositions on SCC VII Tumor Growth

To study the role of ADV compositions in enhancing the efficacy of cytostatic agents, the effect of ADV cytostatic compositions were also tested on a squamous cell carcinoma SCC VII murine tumor, different in histology than RIF-1tumore. Cytostatic compositions were prepared and dosed as described in Tables 12 & 13 with the ethanol/ADV compositions being 70:30 (v/v), respectively. 50 μl of each composition were injected intratumorally into the tumors in a manner analogous to the studies with RIF-1, described previously.

TABLE 12

| Dose of active agent in mg/kg | Composition | 4 × Tumor Growth (days) | |
|---|---|---|---|
| | | treated | untreated |
| none | untreated control | 6.2 ± 0.2 | |
| none | ADV 12 (peanut oil thickened with 15% aluminum monostearate) Placebo | 7.1 ± 0.4 | 6.5 ± 0.2 |
| none | ADV 13 (Sesame Oil/15% Stearic Acid) | 6.9 ± 0.6 | 5.4 ± 0.3 |
| 20 | Etoposide in ADV 12 | 8.7 (2) | 6.1 ± 0.5 |
| 20 | Etoposide in ADV 13 (sesame oil/15% stearic acid) | 8.1 ± 0.7 | 6.5 ± 0.5 |
| 4 | Mitomycin in aqueous suspension | 8.1 ± 0.6 | 6.6 ± 0.6 |
| 4 | Mitomycin in ADV 12 | 8.1 ± 0.4 | 5.6 ± 0.3 |
| 4 | Mitomycin in ADV 13 ethanol solution | 9.9 ± 0.8 | 7.0 ± 0.4 |
| 4 | Cisplatin in ADV 12 | 7.6 ± 1.1 | 5.5 ± 0.3 |
| 4 | Cisplatin in ADV 13 | 10.9 (2) | 6.0 ± 0.3 |
| 2 | Doxorubicin in ADV 12 | 7.2 ± 0.6 | 4.7 ± 0.2 |
| 2 | Doxorubicin in ADV 13 | 6.8 ± 0.7 | 5.2 ± 0.5 |

(2) Indicates that in 2 animals the tumors were still growing when the table was prepared.

The results in Table 12 indicate that etoposide, mitomycin, cisplatin and doxorubicin all exhibit cytostatic activity in lipid matrices such as ADV12 and 13.

A similar study using the SCC VII tumors in mice was performed with compositions containing ethanol and is described in Table 13.

TABLE 13

| Dose of active agent in mg/kg | Composition | 4 × Tumor Growth (Days) | |
|---|---|---|---|
| | | treated | untreated |
| none | untreated control | 5.4 ± 0.1 | |
| none | ADV 12 (peanut oil thickened with 15% aluminum monostearate) ethanol (70/30) | 6.4 ± 0.4 | 6.0 ± 0.2 |
| 12 | Paclitaxel in aqueous suspension | 5.8 ± 0.4 | 5.7 ± 0.4 |
| 12 | Paclitaxel in ADV12/ ethanol | 9.7 ± 0.3 | 5.9 ± 0.3 |
| 20 | Etoposide in aqueous suspension | 7.5 ± 0.2 | 6.5 ± 0.2 |
| 20 | Etoposide in ADV 12/ ethanol | 12.8 ± 1.3 | 7.1 ± 0.8 |
| 4 | Mitomycin in aqueous suspension | 9.4 ± 0.7 | 6.7 ± 0.2 |
| 4 | Mitomycin in ADV 12/ ethanol | 10.9 ± 1.4 | 5.9 ± 0.2 |

The results demonstrate that ADV 12/ethanol compositions enhance the cytostatic effect of paclitaxel, etoposide and mitomycin relative to simple aqueous suspension of these drugs.

Example 10. Alcohol Delivery Vehicles with Paclitaxel

Paclitaxel was dissolved in absolute ethanol, butanol or hexanol at a concentration of 7.5 mg/ml. A dose of 15 mg/Kg was delivered in 0.05 ml of the alcohol drug mixture to the center of the tumor growing in the flank as described previously and the tumor measured. The growth of a second uninjected tumor on the opposing flank of the same mouse was also measured. In addition, the effect of each alcohol on tumor growth was studied by injection of 50 μl of each alcohol into the experimental fibrosarcomas. The results are provided in Table 15.

TABLE 14

Enhancement of Paclitaxel (15 mg/kg) Antitumor Response with Water Immiscible Solvents Administered Intratumorally in RIF-1 Tumors in C3H Mice

| Delivery Vehicle | Water Miscible? | Treated Tumor Growth Delay (Days)/Control Tumor Growth Delay (Days)[†] |
|---|---|---|
| Ethanol | yes | 1.15 |
| Butanol | no | 1.86 |
| Hexanol | no | 1.34 |

[†]Control tumor growth delay corrected for the effect of the test alcohols alone.

The results indicate an increase in antitumor activity of paclitaxel when delivered in the water immiscible solvents, i.e. butanol and hexanol, as compared to ethanol, which is water miscible.

It is evident from the above discussion and results that novel methods and compositions are provided for treating a host with a cellular proliferative disease. By administering cytostatic agents intratumorally in the subject pharmaceutically acceptable, substantially anhydrous, injectable, semi-solid compositions, the activity of the cytostatic agent is enhanced. As the administration of the agent is regional, problems associated with systemic administration are ameliorated if not avoided. Furthermore, many compounds hitherto considered undeliverable or unacceptably toxic or ineffective with conventional delivery modalities find use as cytostatic chemotherapeutic compounds when administered in the subject anhydrous delivery vehicles.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pharmaceutically acceptable, substantially anhydrous, intralesionally injectable, semi-solid cytostatic composition to act as a depot in the treatment of a host with a cellular proliferative disease susceptible to a cytostatic agent, said composition comprising:
   (a) a carrier composition comprising a water immiscible, fatty acid ester matrix; and
   (b) said cytostatic agent in an amount to slow the growth of said cellular proliferative disease.

2. The composition according to claim 1, wherein said fatty acid ester matrix comprises glycerides.

3. The composition according to claim 2, wherein said fatty acid ester matrix is a naturally occurring vegetable oil, a hydrogenated naturally occurring vegetable oil or mixture of hydrogenated naturally occurring vegetable oils, or a thickened naturally occurring vegetable oil.

4. The composition according to claim 3, wherein said cytostatic agent is present in from about 0.5 to 50 mg/ml.

5. The composition according to claim 1, wherein said carrier composition further comprises at least 10(v/v) % of an alkanol of from 2 to 3 carbon atoms.

6. A pharmaceutically acceptable, substantially anhydrous, intralesionally injectable semi-solid cytostatic composition to act as a depot in the treatment of a host with a cellular proliferative disease susceptible to a cytostatic agent, said composition comprising:
   (a) a carrier composition consisting of:
      a water immiscible, fatty acid ester matrix, wherein said fatty acid ester matrix is from 5 to 100 weight % of said carrier composition; and
      an alkanol of from 2 to 3 carbon atoms: and
   (b) said cytostatic agent in an amount to slow the growth of said cellular proliferative disease.

7. The composition according to claim 6, wherein said alkanol is ethanol and is present in from about 30 to 95 (v/v) %.

8. The composition according to claim 6, wherein said fatty acid ester matrix is a naturally occurring vegetable oil, a hydrogenated naturally occurring vegetable oil or mixture of hydrogenated naturally occurring vegetable oils, or a thickened naturally occurring vegetable oil.

9. The composition according to claim 6, wherein said fatty acid ester matrix is a thickened naturally occurring vegetable oil comprising from about 0.5 to 40 (w/v) % of a thickening agent.

10. The composition according to claim 6, wherein said composition further comprises an effector agent.

11. The composition according to claim 10, wherein said effector agent is a vasoconstrictor agent and is epinephrine, eoinephrine borate or ephedrine in from about 0.1 to 2.5 mg/ml.

12. A pharmaceutically acceptable, substantially anhydrous, injectable, semi-solid cytostatic composition to act as a depot in the treatment of a host with a cellular proliferative disease susceptible to a cytostatic agent, having a viscosity in the range of about 5,000 to 50,000 cps at low shear, said composition comprising:
   a carrier composition consisting of:
      a water immiscible, fatty acid ester matrix comprising at least one physiologically acceptable vegetable oil, wherein said fatty acid ester matrix is at least 2 and not more than about 30 weight % of said composition; and
      ethanol in up to 98 v/v % of said composition; and
   said cytostatic agent in an amount to slow the growth of said cellular proliferative disease in the range of about 0.5 to 50 mg/ml.

13. The composition according to claim 12, wherein said physiologically acceptable vegetable oil is selected from the group consisting of peanut, cottonseed, soybean, and sesame oils.

14. The composition according to claim 12, wherein said fatty acid ester matrix is at least 10 (w/v) % of said carrier composition and further comprises a thickening agent selected from the group consisting of triglyceride fatty acids or fatty acid salts of at least 8 carbon atoms, cetyl/stearyl alcohol, wax esters, guar gum, methyl cellulose, hydroxypropyl cellulose and polyethylene glycol 4000.

15. The composition according to claim 12, wherein said cytostatic agent is selected from the group consisting of paclitaxel, mechlorethamine, ionomycin, etoposide, 5-fluorouracil, cantharidin, camptothecin, mitomycin, cisplatin and doxorubicin.

16. The composition according to claim 12, wherein said composition further comprises epinephrine in from about 0.1 to 2.5 mg/ml.

17. A pharmaceutically acceptable, substantially anhydrous, injectable, semi-solid cytostatic composition to act as a depot in the treatment of a host with a cellular proliferative disease susceptible to a cytostatic agent, having a viscosity in the range of about 5,000 to 50,000 cps at low shear, said composition comprising:

a carrier composition comprising:

a water immiscible, fatty acid ester matrix comprising at least one physiologically acceptable vegetable oil, wherein said fatty acid ester matrix is at least 2 and not more than about 95 weight % of said composition; and ethanol in up to 90 v/v % of said composition; and said cytostatic agent in an amount to slow the growth of said cellular proliferative disease in the range of about 0.5 to 50 mg/ml.

18. A composition according to claim 17, wherein said cytostatic agent has a solubility in water under standard temperature and pressure of less than about 0.1% w/v, said cytostatic composition has less than about 1 weight % water, and further comprises 0.1 to 2.5 mg/ml of a vasoconstrictor.

19. A pharmaceutically acceptable, substantially anhydrous cytostatic composition to act as a depot in the treatment of a host with a cellular proliferative disease susceptible to a cytostatic agent, said composition comprising:

a water immiscible alkanol of from 4 to 8 carbon atoms; and said cytostatic agent in an amount to slow the growth of said cellular proliferative disease.

20. The composition according to claim 19, wherein said alkanol is selected from the group consisting of butanol, hexanol and octanol.

21. The composition according to claim 20, wherein said cytostatic agent is paclitaxel.

22. A method for treating a host with a cellular proliferative disease susceptible to a cytostatic agent, said method comprising administering at the site of a lesion of said cellular proliferative disease a pharmaceutically acceptable, substantially anhydrous, injectable, semi-solid cytostatic composition comprising a carrier composition comprising a water immiscible, fatty acid ester matrix; and said cytostatic agent in an amount to slow the growth of said cellular proliferative disease.

23. The method according to claim 22, wherein said fatty acid ester matrix comprises glycerides.

24. The method according to claim 23, wherein said fatty acid ester matrix is a naturally occurring vegetable oil, a hydrogenated naturally occurring vegetable oil or mixture of hydrogenated naturally occurring vegetable oils, or a thickened naturally occurring vegetable oil.

25. The method according to claim 24, wherein said cytostatic agent is present in from about 0.5 to 50 mg/ml.

26. The method according to claim 23, wherein said carrier composition further comprises at least 10(v/v) % of an alkanol of from 2 to 3 carbon atoms.

27. A method for treating a host with a cellular proliferative disease susceptible to a cytostatic agent, said method comprising administering at the site of a lesion of said cellular proliferative disease a pharmaceutically acceptable, substantially anhydrous, injectable, semi-solid cytostatic composition comprising a carrier composition consisting of: a water immiscible, fatty acid ester matrix, wherein said fatty acid ester matrix is present in said composition in an amount from 10 to 90 weight %, and an alkanol selected from the group consisting of ethanol and isopropanol, wherein said alkanol is present in an amount from 10 to 90 v/v %; and said cytostatic agent in an amount to slow the growth of said cellular proliferative disease.

28. The method according to claim 27, wherein said method further comprises administration of a vasoconstrictor agent at the site of said lesion.

29. The method according to claim 28, wherein said vasoconstrictor agent is administered prior to administration of said cytostatic composition.

30. The method according to claim 29 wherein said vasoconstrictor is administered concurrently with said cytostatic composition.

31. A method of treating a host with a cellular proliferative disease susceptible to a cytostatic agent, said method comprising administering at the site of a lesion of said cellular proliferative disease a composition comprising a water immiscible alkanol of from 4 to 8 carbon atoms and a said cytostatic agent in an amount to slow the growth of said cellular proliferative disease.

32. The method according to claim 31, wherein said water immiscible alkanol is selected from the group consisting of butanol, hexanol and octanol and said cytostatic agent is paclitaxel.

33. A method for treating a host with a neoplastic disease susceptible to a cytostatic agent, said method comprising administering at the site of a lesion of said neoplastic disease a pharmaceutically acceptable, substantially anhydrous, injectable, semi-solid cytostatic composition comprising a carrier composition comprising a water immiscible, fatty acid ester matrix; and said cytostatic agent in an amount to slow the growth of said neoplastic disease.

34. The method according to claim 33, wherein said fatty acid ester matrix comprises glycerides.

35. The method according to claim 34, wherein said carrier composition further comprises at least 10 (v/v) % of an alkanol of from 2 to 3 carbon atoms.

36. The method according to claim 33, wherein said cytostatic agent is present in from about 0.5 to 50 mg/ml.

* * * * *